United States Patent [19]

LeFevre et al.

[11] 4,037,596

[45] July 26, 1977

[54] PARENTERAL ADMINISTRATION SET WITH INTERNAL VALVE AND FLOW RESTRICTOR

[75] Inventors: Robert J. LeFevre; George K. Burke; Kenneth Raines, all of Bethlehem, Pa.

[73] Assignee: Burron Medical Products, Inc., Bethlehem, Pa.

[21] Appl. No.: 637,209

[22] Filed: Dec. 3, 1975

[51] Int. Cl.² ............................................. A61M 5/16
[52] U.S. Cl. ........................... 128/214 C; 128/214.2; 138/44
[58] Field of Search .......... 128/214 R, 214 C, 214 E, 128/214 F, 214.2, DIG. 12, DIG. 13; 251/123–125, 139, 141; 137/486, 487.5; 222/52, 59, 420, 422; 138/40, 44–45

[56] References Cited

U.S. PATENT DOCUMENTS

| | | | |
|---|---|---|---|
| 2,096,808 | 10/1937 | Jenkins et al. | 251/141 |
| 2,254,833 | 9/1941 | Ashbenaz | 128/213 |
| 2,837,091 | 6/1958 | McMinn et al. | 128/214 C |
| 3,675,891 | 7/1972 | Reynolds et al. | 128/214 F |
| 3,828,818 | 8/1974 | Hunt | 251/141 X |
| 3,878,869 | 4/1975 | Yamanouchi et al. | 138/40 |
| 3,890,968 | 6/1975 | Pierce et al. | 128/214 E |

FOREIGN PATENT DOCUMENTS

| | | | |
|---|---|---|---|
| 1,258,222 | 3/1961 | France | 128/214 C |

*Primary Examiner*—Dalton L. Truluck
*Attorney, Agent, or Firm*—Shoemaker and Mattare, Ltd.

[57] ABSTRACT

A parenteral administration set, particularly for intravenous infusion of fluids, includes a drip chamber and a length of flexible intravenous tubing connected therewith. A flow controlling valve is in the length of tubing and is operable between open and closed positions from exteriorly of the tubing to obtain a desired drip rate corresponding directly with the frequency of valve operation. A fixed flow restrictor is in the length of tubing to impart a predetermined back pressure to flow through the set, whereby the rate of drop formation in the drip chamber is controlled to a value to insure that only one drop will form and fall for each valve opening.

14 Claims, 6 Drawing Figures

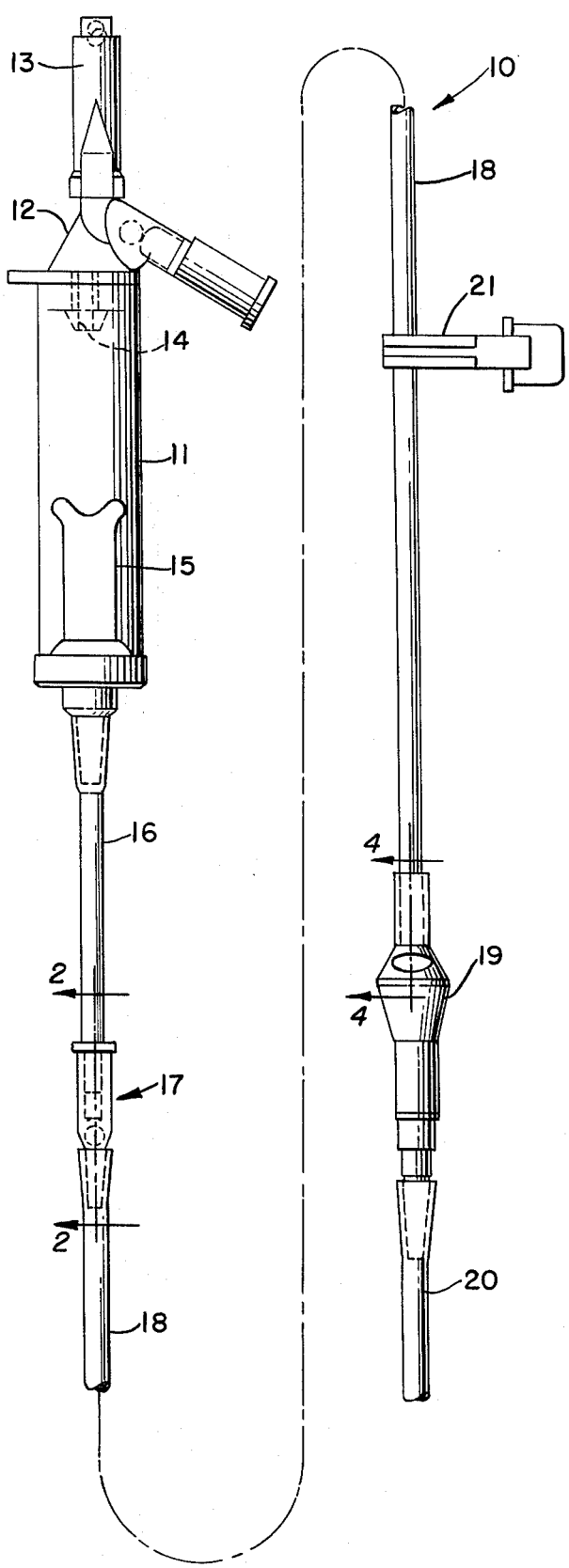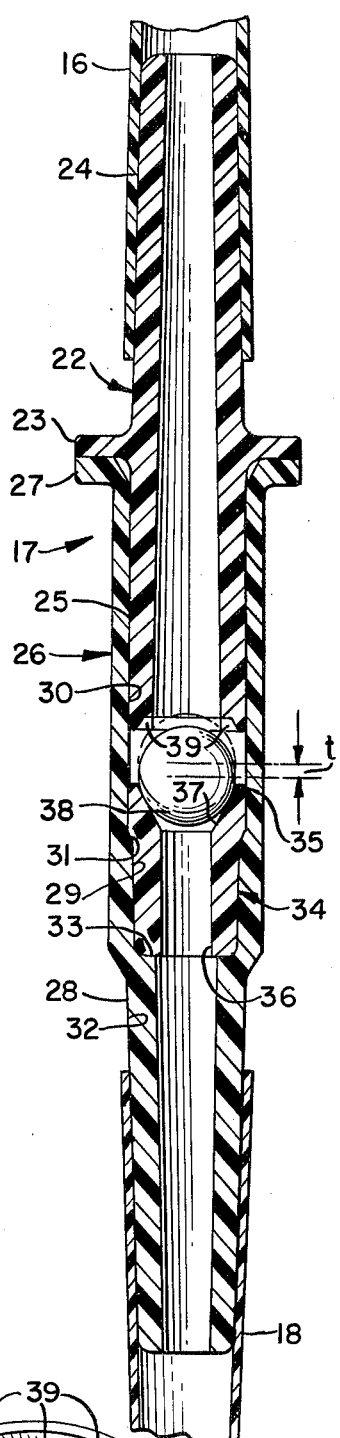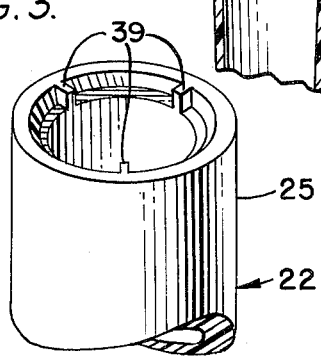

PARENTERAL ADMINISTRATION SET WITH INTERNAL VALVE AND FLOW RESTRICTOR

BACKGROUND OF THE INVENTION

This invention relates to parenteral administration sets, and more particularly, to an intravenous set for administering fluids intravenously.

Even more specifically, the present invention relates to a disposable intravenous administration set including a drip chamber of substantially conventional construction having means theron for connection with a source of IV fluid, a length of flexible IV tubing connected with the drip chamber, valve means in the length of tubing operable from exteriorly of the tubing to open and closed positions to obtain a desired drip rate through the drip chamber and thus obtain a desired flow rate through the set, and wherein a fixed restrictor is in the length of tubing to impart a predetermined back pressure to flow therethrough to thus regulate, at least to an extent, the time it takes a drop to form in the drip chamber and thereby insure that only one drop will form and fall for each cycle of valve operation, at least for normal operating ranges, and preferably from about 1 drop per minute up to about 99 drops per minute.

In the prior art, many different types of intravenous and parenteral administration sets are known. Many such sets are controlled by valve means, and some even have internal valve means. However, with the prior art intravenous administration sets, there is no means provided to regulate the rate of drop formation to insure that only one drop will form and fall during the time that the control valve is open. In other words, it is frequently necessary to use different needle sizes, depending upon th type of fluid being administered and the urgency with which a prescribed amount of fluid must be introduced into a patient's veins, and if the size or gauge of the needle used is no larger than about 20 or 21 gauge, the rate of drop formation will be regulated so that only one drop will form and fall for each opening cycle of the valve, so long as the valve cycle is within normal operating ranges.

However, when a larger bore needle is used with the prior art sets, there is practically no back pressure on the system, and the set is operating essentially as an open flow set, and accordingly, when the valve opens, there is no regulation of the rate of drop formation and more than one drop may form and fall during the time the valve is open. Accordingly, accurate regulation of drop rate and thus flow rate through the prior art sets cannot be obtained with all needle sizes likely to be used with the set.

With the present invention, having the unique internal valve and fixed restrictor, as noted above, the rate of drop formation is regulated due to the back pressure imposed on the system by the restrictor, and accordingly, the rate of drop formation is such that only one drop will form and fall during a cycle of operation of the valve regardless of the size of needle used on the set.

Objects of the Invention

Accordingly, it is an object of this invention to provide a parenteral administration set having restrictor means therein, whereby a back pressure is produced in the system such that only one drop forms and falls during a cycle of valve operation.

Another object of the invention is to provide an intravenous administration set having a drip chamber and length of flexible tubing connected therewith, and wherein a valve means is in the tubing to control flow through the set and restrictor means is disposed in the tubing to impart a prescribed back pressure to flow through the system, whereby only one drop will form and fall for each cycle of operation of the valve.

A still further object of the invention is to provide an intravenous administration set having an internal valve therein having a predetermined length of travel between its closed and fully open positions, whereby the valve is enabled to close after a drop forms and falls and before a subsequent drop can form and fall.

BRIEF DESCRIPTION OF THE DRAWINGS

FIG. 1 is a somewhat schematic view in elevation, with portions broken away, of an intravenous administration set in accordance with the invention.

FIG. 2 is a greatly enlarged, fragmentary view in elevation taken along line 2—2 in FIG. 1.

FIG. 3 is a further enlarged, fragmentary, perspective view of the end of the valve body inlet portion comprising the stop for limiting the opening travel of the ball valve.

DETAILED DESCRIPTION OF THE PREFERRED EMBODIMENTS

Figure 4:
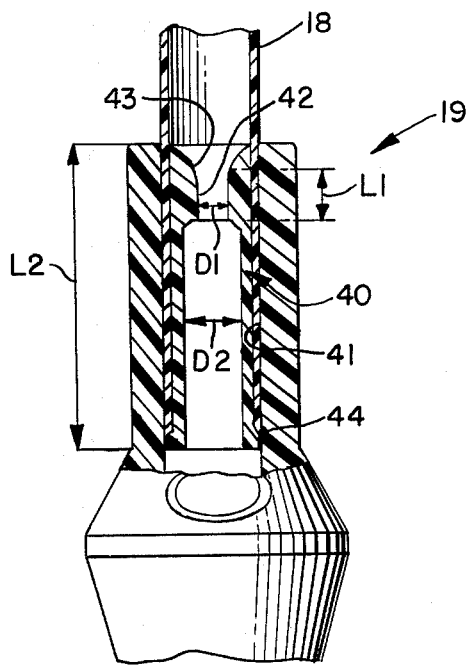
FIG. 4 is an enlarged, fragmentary view in section of the restrictor used in the set of the invention, and is taken along line 4—4 in FIG. 1.

In the drawings, wherein like reference numerals indicate like parts throughout the several views, an intravenous administration set in accordance with the invention is indicated generally at 10, and comprises a drip chamber 11 of substantially conventional construction, and as seen in FIG. 1, the drip chamber has a dual flow piercing device 12 attached thereto for connection with a source of intravenous fluid. The piercing device 12 has a guard 13 thereon, and the drip chamber 11 has a drop forming orifice 14 at the upper end thereof for forming drops of a predetermined size, and a filter 15 is in the lower end of the drip chamber for filtering contaminants from the fluid. This filter serves to filter out particles which might interfere with proper valve operation.

A length of IV tubing 16 is connected with the outlet from the drip chamber 11 and extends to a valve means 17. a further length of IV tubing 18 extends from the valve means 17 to a connector or needle adaptor or the like 19, having a suitable guard 20 with cotton or the like therein on the outlet end thereof. A suitable clamp 21 is on the length of tubing 18 between the ends thereof for providing shut-off of flow through the set or effecting control of flow of fluid therethrough, if desired or necessary.

As seen in FIGS. 2 and 3, the valve means 17 comprises an inlet body portion 22 of impact styrene or other suitable material, and having a radially outwardly extending flange 23 thereon substantially intermediate the ends thereof and defining an axially extending inlet end portion 24 and an oppositely extending outlet end portion 25. The inlet end portion 24 is inserted into the end of the length of tubing 16 and secured thereto by means of a suitable adhesive or solvent and the like, as is known in the prior art. The outlet end portion 25 is snugly received in the open end of an outlet body portion 26, having a radially outwardly extending flange 27 on the inlet end thereof, which may be suitably sealed and secured to the flange 23 on the inlet portion 22, as by means of a sonic weld or the like. The outlet body portion 26 has a reduced diameter outlet end 28 and a reduced diameter intermediate bore portion 29 joined with the inlet bore portion 30 at a tapered shoulder 31. The inner bore through the outlet body portion 26 is further reduced to define an outlet bore portion 32 joined with the intermediate bore portion 29 by a shoulder 33. The length of tubing 18 is received over and suitably secured to the outlet end portion 28 of outlet body portion 26.

A valve seat insert 34 is secured in the intermediate bore portion 29 and has one end thereof engaged against the shoulder 33, and a radially enlarged inlet end 35 engaged against tapered shoulder 31. The seat insert 34 has a bore 36 therethrough of slightly less diameter than the outlet bore 32 in the valve body outlet portion 26, and the seat insert has a tapered, frusto-conically shaped seating surface 37 subtending an angle of approximately 60°, and dimensioned such that a steel ball 38 having a diameter of approximately 0.125 inches engages the seat with the ball radius extending perpendicular to a tangent at the point of engagement of the ball with the seat.

The end of inlet body portion 22, disposed adjacent the seat insert 34, is spaced from the seat insert a distance such that for a ball having a diameter of approximately 0.125 inches, the ball has a travel of 0.015 inches between its closed and fully opened positions. Valve stops 39 are formed on the end of the inlet body portion 22 to engage the ball and limit its opening travel while permitting flow therepast.

In this form of the invention, a clearance of approximately 0.019 inches is provided between the outer diameter or surface of the ball and the adjacent inner surface of the outlet body portion 26.

The outlet body portion 26 may be formed of general purpose styrene or other suitable materials, as desired, and the seat insert 34 is preferably made of soft gum rubber, such as natural latex or the like. The valve ball 38 preferably is made of steel or other suitable material, and with the soft rubber insert as provided in this form of the invention, the manufacturing tolerances of the ball and seat are not as critical, since the resiliency of the seat will enable the ball to be pressed thereinto, thus sealing against flow even in the event of slight surface irregularities in either of the ball or seat.

The connector or needle adaptor or the like 19 is shown in FIG. 4, and a restrictor 40 is press fitted into the end of the length of tubing 18, and the end of the tubing 18, with the restrictor 40 therein, is suitably secured in the inlet bore 41 of the connector 19.

The restrictor 40 has an orifice 42 formed in the inlet end thereof, with a predetermined diameter D1 and length L1 and a rounded inlet 43 thereto. The bore is enlarged to a diameter D2, which extends over the remainder of the total length L2 of the restrictor 40, and the outlet end of the restrictor has a radially enlarged flange 44 thereon, thus abuts against the end of the length of tubing 18 when the restrictor is operatively positioned in the tubing 18. The restrictor 40 is preferably made of a material such as polypropylene or the like, but it may be made of any other suitable material.

In a preferred construction of the invention, the length L1 and diameter D1 of the orifice 42 are about 0.062 inches and 0.020 inches, respectively, and the rounded inlet end 43 thereto has a radius of curvature of about 0.081 inches. The overall length L2 of the restrictor is about 0.50 inches, and the outlet bore has a diameter D2 of about 0.068 inches. With these dimensions, it has been found in practice that an accurate drop rate can be obtained, regardless of the size of needle used with the set, since the orifice 42 imparts a back pressure on the system sufficient to inhibit or restrict flow through the system such that the rate of drop formation is controlled to a degree such that only one drop forms and falls for one cycle of valve operation at any normal or usually encountered frequency of operation of the valve, and yet the orifice is not so small that it inhibits the rate of drop formation to a point whereat a drop is not enabled to form and fall within normal operating ranges of the valve.

Figure 6:
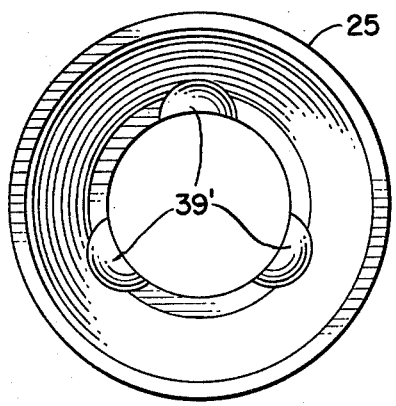
FIG. 6 is a plan view of the end of the inlet portion of the valve body of FIG. 5, showing the valve engaging stop means thereon.
Figure 5:
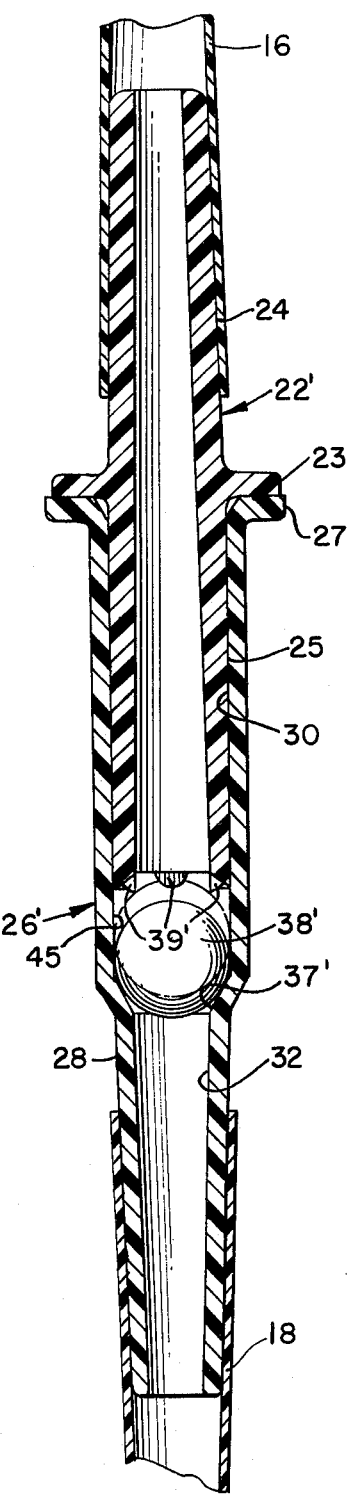
FIG. 5 is a view similar to FIG. 2 of a modified valve means.

A modified valve 17' is illustrated in FIGS. 5 and 6, and is generally similar to that form of the invention in FIGS. 2 and 3, and includes an inlet body portion 22' and outlet body portion 26'. However, in this form of the invention, the valve seat 37' is formed integrally with the outlet valve body portion 26'. Moreover, in this form of the invention, the inlet bore 45 tapers outwardly towards the inlet approximately 1°, and has a slightly larger diameter than the diameter of the ball 38'. Additionally, the ball limit stops 39' are slightly differently shaped than those previously described. In all other respects, this form of the invention is substantially identical to that previously described.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

We claim:

1. A parenteral administration set comprising: a drip chamber having means thereon for connection with a source of fluid to be administered and having orifice means for forming drops of fluid flowng from the drip chamber; a length of flexible tubing connected with the drip chamber; valve means having movable means therein and in fluid communication with the interior of the length of tubing and operable between open and closed positions from exteriorly of the tubing to obtain a desired drip rate and thus control flow through the set; a needle adaptor connected with the tubing at its opposite end for receiving flow from the valve means; and fixed restrictor means in the tubing separate from the valve means and having an internal bore with a predetermined length and diameter sized to impart restriction to flow therethrough approximating the restriction to flow imposed by a needle of no larger than about 20 or 21 gauge, to insure that the rate of drop formation is such that only one drop will form and fall for each opening cycle of the valve means during normal operation, regardless of the size of needle connected to the needle adapter.

2. A parenteral administration set as in claim 1, wherein said restrictor means is in the needle adapter.

3. A parenteral administration set as in claim 2, wherein the restrictor means comprises an elongate tubular body having an orifice therein, said body snugly received in the end of the length of tubing, and said end of the tubing received in a bore in the needle adapter.

4. A parenteral administration set as in claim 3, wherein the orifice has a diameter of about 0.020 inch and a length approximately three times the diameter.

5. A parenteral administration set as in claim 4, wherein the tubular body has a length of about 0.500 inch, and has an inlet end and an outlet end, said orifice being in the inlet end thereof.

6. A parenteral administration set as in claim 5, wherein the orifice has a rounded inlet end.

7. A parenteral administration set as in claim 4, wherein the valve means comprises a valve body secured in the length of tubing and having a valve seat between the ends thereof, a valve ball confined within the valve body and reciprocable between open and closed positions relative to the seat, and limit stop means to limit the opening travel of the ball to an amount less than the diameter of the orifice.

8. A parenteral administration set as in claim 1, wherein the valve means comprises a valve body secured in the length of tubing, and having a valve seat between the ends thereof, and a valve ball confined within the valve body and reciprocable between open and closed positions relative to said seat, said valve body comprising secured together inlet and outlet body portions, one of said portions having the valve seat thereon.

9. A parenteral administration set as in claim 8, wherein a valve stop means is on the other of said valve body portions in a position to be engaged by the ball to limit the opening travel of the ball.

10. A parenteral administration set as in claim 9, wherein the restrictor means has an orifice with a predetermined diameter and length, and the opening travel of the valve ball is less than the diameter of the orifice.

11. A parenteral administration set as in claim 8, wherein the valve seat is formed integrally with the valve body and comprises a relatively hard material.

12. A parenteral administration set as in claim 8, wherein the valve comprises an inset in the valve body and is made of relatively soft material.

13. A parenteral administration set as in claim 11, wherein the valve seat is made of general purpose styrene and the valve ball is made of magnetic material.

14. A parenteral administration set as in claim 12, wherein the valve seat insert comprises gum rubber and the valve ball is made of magnetic material.

* * * * *